(12) United States Patent
Jansen

(10) Patent No.: US 6,533,814 B1
(45) Date of Patent: Mar. 18, 2003

(54) INTRAOCULAR LENS HAVING A DESIGN FOR CONTROLLING ITS AXIAL DISPLACEMENT AFTER IMPLANTATION

(75) Inventor: Peter Jansen, Uithuizen (NL)

(73) Assignee: Pharmacia Groningen, BV, Groningen (NL)

( * ) Notice: Subject to any disclaimer, the term of this patent is extended or adjusted under 35 U.S.C. 154(b) by 0 days.

(21) Appl. No.: 09/674,133

(22) PCT Filed: May 3, 1999

(86) PCT No.: PCT/EP99/03037

§ 371 (c)(1),
(2), (4) Date: Jan. 16, 2001

(87) PCT Pub. No.: WO99/56669

PCT Pub. Date: Nov. 11, 1999

(30) Foreign Application Priority Data

May 5, 1998 (SE) ................................................ 9801573

(51) Int. Cl.⁷ .................................................. A61F 2/16
(52) U.S. Cl. ....................... 623/6.43; 623/6.4; 623/6.38
(58) Field of Search ............................... 623/6.11, 6.38, 623/6.4, 6.43

(56) References Cited

U.S. PATENT DOCUMENTS

| | | |
|---|---|---|
| 3,925,825 A | 12/1975 | Richards et al. |
| 4,363,143 A | 12/1982 | Callahan |
| 4,573,998 A | 3/1986 | Mazzocco |
| 4,778,464 A | 10/1988 | Sergienko et al. |
| 5,160,345 A | 11/1992 | Bragg |
| 6,197,059 B1 * | 3/2001 | Cumming ................... 623/6.39 |
| 6,221,106 B1 * | 4/2001 | Hermeking ................. 623/6.4 |

FOREIGN PATENT DOCUMENTS

| | | |
|---|---|---|
| DE | 2437184 | 2/1975 |
| DE | 2538983 | 7/1976 |
| EP | 0154655 | 9/1985 |
| EP | 0336877 | 11/1989 |
| GB | 1449572 | 9/1976 |
| GB | 2164561 | 3/1986 |
| WO | WO9727825 | 8/1997 |

OTHER PUBLICATIONS

Läkartidningen, *Artificiell Ögonlins Vid Afaki–Indikationer Och Komplikationer*, 81(16):1614 (Apr. 1984).

* cited by examiner

*Primary Examiner*—Dinh X. Nguyen
(74) *Attorney, Agent, or Firm*—Dinsmore & Shohl LLP

(57) ABSTRACT

Intraocular lens comprising a central optical body and haptics attached to or formed integrally with said optical body wherein the haptics are attached to the optical body via connecting members separating the haptic plane from the optical plane by a distance b which is at least half the thickness of the optical body.

22 Claims, 1 Drawing Sheet

INTRAOCULAR LENS HAVING A DESIGN FOR CONTROLLING ITS AXIAL DISPLACEMENT AFTER IMPLANTATION

FIELD OF INVENTION

The present invention relates to the field of intraocular lenses (IOLs) and more specifically to a new lens with an improved haptics design for controlled or predictable axial displacement of the optical body in the capsular bag after implantation.

BACKGROUND OF THE INVENTION

The traditional IOL comprises an optical body and haptics attached to the optical body or the haptics being integrally formed from the same piece of material as the optical body. Polymethylmethacrylate (PMMA) was early found to be an excellent material for such lenses, and especially for the lens body, due to good optical characteristics and good biocompatibility. Considerable efforts have been focused on the haptics design for a number of reasons: the tissue in the eye being rather sensitive to external forces and it is important that the optical axis of the lens body is kept centered in the eye, just to mention a couple of aspects to be considered. This fact is well illustrated by the great number of patents published over the years and which are related to various haptics designs.

In preparation for lens implantation the natural lens is removed from the capsular bag and the bag in most cases is filled with a high viscosity solution, e.g. Healon® (Pharmacia & Upjohn AB). Then the lens is implanted through an incision, via iris, into the capsular bag and positioned with the haptics contacting the wall of the bag and centering the optical body behind the iris. In order to avoid that the optical body contacts the iris it is common practice that the haptics have a certain forward angulation. e.g. around 5–10 degrees, relative to the optical body. After implantation when the haptics are somewhat compressed in the bag, the lens vaults backwards towards the posterior capsular wall, which in most cases remains after removal of the natural lens. Since the size of the bag differs among the patients requiring a new artificial lens, it is easy to realize that the position of the optical body will differ from one individual to another.

Certain dimensions of the eye, including the position of the capsular bag are measured prior to surgery to give an appropriate basis for a calculation of the dioptre of the IOL to be implanted. If the axial position of the lens body is not completely predictable an error is introduced which is as high as around 0.2 D for each 0.1 mm displacement. Therefore, there is a need for lenses which during implantation are placed in a predicted position and which remain in that position. An improved method for calculation of the correct dioptre is disclosed in pending patent application EP96914495.5. An important parameter is the position of the haptic plane which can be derived from measurements by the ophthalmologist in preparation for surgery, but it is important to consider the effect of the vault resulting from the compression of the haptics. Supporting elements of the implantable lens, i.e. haptics, are well disclosed in the literature for different purposes. For example U.S. Pat. No. 4,778,464 discloses an IOL with supporting elements at a controlled distance form its optic part which together with two rods will interpose the iris. This type of lens is to be fixated by the iris and is of a different type to those disclosed above and which are the subject of the present invention and aimed to be implanted in the capsular bag. Some other IOLs of the iris fixation type are disclosed by the German patent specification DE 2437184 and DE 2538983.

It is a demand for an IOL to be placed in the capsular bag which provides a better optical outcome after cataract surgery irrespectively of the size of the capsular bag or the vitreous pressure which vary considerably between different patients.

DESCRIPTION OF THE INVENTION

Figure 1:
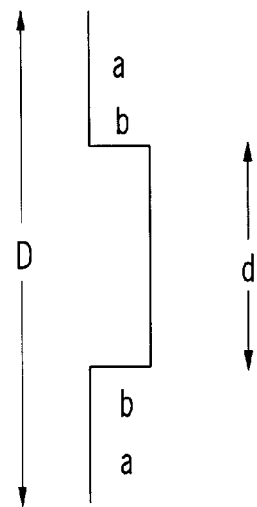
FIG. 1 is a schematic diagram of a lens according to the invention.

We have now found that a controlled or predictable displacement of the optic along the optical axis, as a result of compression forces acting on the haptics and the reaction force from the vitreous body, is achieved by intraocular lenses having parallel optic and haptic planes displaced a suitable distance to each other, as is illustrated in FIG. 1. The over diameter D of the lens is generally in the range of 7–15 mm and the diameter d of the optics 4–8 mm. The projected length of the haptic being defined as a which is equal to (D–d)/2. The two identical lateral parts of the haptic together constitute the haptic plane. The characterizing feature of the new design is the connecting member b by which the haptic plane is displaced a distance b from the optical plane. In the schematic presentation given in FIG. 1 this connecting member is presented as being mainly parallel to the optical axis, that is substantially perpendicular to the plane of the optics as well as the plane of the haptics. However, the important characteristic is the distance that is created between the haptic plane and the plane of the optical body in order to avoid contact with the iris it should preferably be larger than half the thickness of the optics. In general IOLs are up to about 2 mm thick and it can therefore be concluded that b in most cases would be in the range of 0.2 to 1.0 mm.

It is further realized that the stiffness of the haptic parts a (haptic) and b (connecting member), or more correctly the stiffness ratio between a and b, is of importance to accomplish a predictable displacement. Assuming a maximum vault of 0.01 mm to be acceptable. we can conclude that with the already defined geometry of the lens combined with the geometry of the capsular bag, the minimum stiffness ratio a to b is found to be about 1 to 12.

Figure 2:
FIG. 2 is a plan view of a lens according to the invention.

While the connecting member very well also in practice could have the schematic design given in FIG. 1 it is obvious to a person skilled in the art that modified connecting members, especially with smooth bends, can be utilized as long as the key feature of separating the haptic plane from the optical plane is achieved. One further embodiment of the present invention is shown in FIG. 2.

Lenses according to the invention can be made of rigid material like PMMA as well as other biocompatible, foldable materials, like hydrogels, soft acrylics, urethanes, and combinations of these material.

The haptics are in one embodiment of the invention formed from the same piece of material as the optical body, e.g. PMMA, which means that they are connected integrally with said body in what is often referred to as a one-piece lens. In another embodiment the haptics are formed from a different material compared to the optics and attached by methods know per se, for instance by plasma or corona discharge bonding, clamping, polymerization or glueing. In these so called three-piece lenses the optics could be prepared from a stiff material like PMMA, but preferably of a foldable material.

What is claimed is:

1. Intraocular lens comprising a central optical body and two haptics attached to or formed integrally with said optical body, wherein the haptics are adapted to contact the capsular bag of an eye and center the optical body behind the iris of the eye to avoid contact of the lens with the iris, wherein the haptics are respectively attached to the optical body via two connecting members separating the haptic plane from the optical plane by a distance b which is larger than half the thickness of the optical body, and wherein each connecting member is substantially perpendicular to the optic plane of the lens.

2. Intraocular lens according to claim 1, wherein the lens is a one-piece lens manufactured from PMMA.

3. Intraocular lens according to claim 1, wherein the lens is a one-piece lens prepared from a foldable material.

4. Intraocular lens according to claim 1, wherein the lens is a three-piece foldable lens.

5. Intraocular lens according to claim 1, wherein the lens is adapted to exhibit no displacement of the optical body along the optical axis as a result of compression forces and reaction force from a vitreous body acting on the haptics in the capsular bag after implantation.

6. Intraocular lens according to claim 1, wherein the stiffness ratio of the haptic to the connecting members is about 1:12.

7. Intraocular lens according to claim 1 wherein the lens includes a haptic plane and an optic plane, and the haptic plane and the optic plane of the lens are parallel.

8. Intraocular lens according to claim 1 wherein the haptics comprise two identical lateral parts.

9. Intraocular lens according to claim 2, wherein the lens is adapted to exhibit no displacement of the optical body along the optical axis as a result of compression forces and reaction force from a vitreous body acting on the haptics in the capsular bag after implantation.

10. Intraocular lens according to claim 3, wherein the lens is adapted to exhibit no displacement of the optical body along the optical axis as a result of compression forces and reaction force from a vitreous body acting on the haptics in the capsular bag after implantation.

11. Intraocular lens according to claim 4, wherein the lens is adapted to exhibit no displacement of the optical body along the optical axis as a result of compression forces and reaction force from a vitreous body acting on the haptics in the capsular bag after implantation.

12. Intraocular lens according to claim 1, wherein the haptics are attached to the edge of the optical body via the connecting members.

13. Intraocular lens according to claim 1, wherein the connecting members are diametrically opposed to one another.

14. Intraocular lens comprising a central optical body and haptics attached to or formed integrally with said optical body, wherein the haptics are adapted to contact the capsular bag of an eye and center the optical body behind the iris of the eye to avoid contact of the lens with the iris, wherein the haptics are attached to the optical body via connecting members separating the haptic plane from the optical plane by a distance b which is larger than half the thickness of the optical body, and wherein each connecting member is substantially perpendicular to the optical plane of the lens, whereby a controlled or predictable displacement of the intraocular lens is achieved in the eye.

15. Intraocular lens according to claim 14, wherein the stiffness ratio of the haptic to the connecting members is about 1:12.

16. Intraocular lens according to claim 14, wherein the haptic plane is perpendicular to the optical axis of the lens.

17. Intraocular lens according to claim 14, wherein the lens is a one-piece lens manufactured from PMMA.

18. Intraocular lens according to claim 14, wherein the lens is a one-piece lens prepared from a foldable material.

19. Intraocular lens according to claim 14, wherein the lens is a three-piece foldable lens.

20. Intraocular lens according to claim 14, wherein the lens is adapted to exhibit no displacement of the optical body along the optical axis as a result of compression forces and reaction force from a vitreous body acting on the haptics in the capsular bag after implantation.

21. Intraocular lens according to claim 14, wherein the haptics comprise two identical lateral parts.

22. Intraocular lens according to claim 14, wherein the haptics are attached to the edge of the optical body via the connecting members.

* * * * *